(12) United States Patent
Bramlage et al.

(10) Patent No.: US 6,398,746 B2
(45) Date of Patent: Jun. 4, 2002

(54) SHOULDERS STABILIZING BRACE

(76) Inventors: Meghan Bramlage, 102 Ashford Ct., Wexford, PA (US) 15090; Patti J. Hunker, 12408 Traverse Pl., Fishers, IN (US) 46038

( * ) Notice: Subject to any disclaimer, the term of this patent is extended or adjusted under 35 U.S.C. 154(b) by 0 days.

(21) Appl. No.: 09/909,598

(22) Filed: Jul. 20, 2001

Related U.S. Application Data

(60) Provisional application No. 60/220,523, filed on Jul. 21, 2000.

(51) Int. Cl.[7] .................................................. A61F 5/00
(52) U.S. Cl. ............................... 602/5; 602/20; 128/869
(58) Field of Search ......................... 602/4, 5, 20, 61, 602/62; 128/869, 874, 877; 2/44, 45

(56) References Cited

U.S. PATENT DOCUMENTS

| | | | | |
|---|---|---|---|---|
| 4,564,008 A | * | 1/1986 | Donahoo | 602/4 |
| 5,358,470 A | * | 10/1994 | Johnson | 602/20 |
| 5,628,725 A | * | 5/1997 | Ostergard | 602/62 |
| 5,830,165 A | * | 11/1998 | Rowe et al. | 602/4 |
| 6,030,354 A | * | 2/2000 | Lakusiewicz | 602/4 |
| 6,099,489 A | * | 8/2000 | Herzberg et al. | 602/4 |
| 6,106,493 A | * | 8/2000 | Rozell | 602/20 |
| 6,110,133 A | * | 8/2000 | Ritts | 602/4 |

* cited by examiner

*Primary Examiner*—Michael A. Brown
(74) *Attorney, Agent, or Firm*—Clifford W. Browning; Woodard, Emhardt, Naughton, Moriarty & McNett

(57) ABSTRACT

The present invention includes a brace for supporting a wearer's shoulder joint during movement. The brace is of one-piece construction and preferably from a stretchable material. The brace is comprised of five components: the body sleeve, the inferior strap mechanism (axillary strap), the axillary pouch, and the compression strap (deltoid strap). The sleeve is sewn on the involved shoulder. It extends from the deltoid insertion to the base of the neck. The sleeve component extends across the mid-thorax, just below the pectoral region. It is secured just inferior to the axillary region of the opposite shoulder. The uninvolved shoulder and the neck are exposed. The axillary pouch which is comprised of a thinner material, is sewn into the axillary region along the underside of the sleeve and body component. The axillary pouch narrows into the axillary straps. This creates a sling-like mechanism to support the inferior capsule. Through equal pressure directed superiorly, the straps are positioned in a criss-cross fashion over the acromioclavicular joint. They are then secured in the mid-thoracic spine and mid-sternal regions. The deltoid strap is sewn to the sleeve in the mid-deltoid region. Pressure is applied evenly through each end of the strap to provide compression to the glenohumeral joint. The straps are directed slightly in an inferior direction and are secured crossing the midline of the sternum and thoracic spine.

11 Claims, 4 Drawing Sheets

SHOULDERS STABILIZING BRACE

This application claims the benefit of co-pending U.S. Provisional Patent Application Ser. No. 60/220,523, filed Jul. 21, 2000.

FIELD OF THE INVENTION

The present invention relates to orthopedic braces for glenohumeral joint support.

BACKGROUND OF THE INVENTION

The glenohumeral joint is invariably unstable due to the convex articulation of the humeral head with the concavity of the glenoid fossa. In any anatomical direction, the humeral head is only covered by 25-30% of the glenoid surface. The joint receives support statically, dynamically, and by negative pressure. The soft tissues such as the glenohumeral ligaments, labrum and capsule as well as the articular surface provide static support. Disruption of the static restraints either due to trauma or inherent joint laxity may lead to a reduction of "load sharing." The ligaments are unable to effectively resist joint translation, which increases joint stability. Specifically, the inferior glenohumeral ligament is the most important component of the complex. In a study done by R. E. Schwartz, S. J. O'Brien, P. A. Torzilli and R. F. Warren entitled, "Capsular restraints to anterier-posterier motion of the shoulder," *Trans Orthop Res Soc* 12:78, 1987., the inferior glenohumeral ligament was found to be the primary check against both anterior and posterior translation with the shoulder abducted. S. J. O'brien, M. C. Neves and S. P. Anroczky, "The anatomy and histology of the inferior glenohumeral ligament complex of the shoulder," *Am J Sports Med* 18(5) 449–456, 1990., concludes from their study that the inferior glenohumeral ligament not only provides support in abduction but also with combined motions of internal and external rotation. The authors suggest that reestablishing the integrity of the inferior glenohumeral ligament may be an important consideration when treating anterior and posterior instabilities.

Dynamic support is provided by the rotator cuff (subscapularis, supraspinatus, infraspinatus, teres minor) and deltoid musculature. The dynamic stabilizers act as barriers to help resist translation and indirectly by moving the joint into a position that tightens the capsuloligamentous structures. Force couples are produced by the subscapularis with counterbalance from the infraspinatus/teres minor muscles in the transverse plane and in the coronal plane by the deltoid counterbalanced by the infraspinatus and teres/minor.

Bracing may become necessary to those who have shoulder instability due to trauma, failed surgical intervention or inherent joint laxity. Providing external dynamic support may allow the individual to return to their previous level of function while possibly reducing the risk of further injury. Previously devised shoulder braces have addressed instability in the anterior and posterior directions but have not addressed the importance of inferior capsular reinforcement or glenohumeral joint compression.

SUMMARY OF THE INVENTION

The present invention comprises a brace for supporting a wearer's shoulder joint during movement. The brace is of one-piece construction and preferably from a stretchable neoprene, loop type material. It provides support to the glenohumeral joint inferiorly as well as joint compression following compromise of the static restraining structures. The present invention can functionally stabilize and assist the individual according to their specific needs during rehabilitation, activities of daily living or sport participation.

The present stabilizing system grips the wearer's skin so that it can provide support and compression to the shoulder joint. The shoulder-stabilizing device comprises a garment that includes a chest component, shoulder component, axillary component and upper arm (sleeve) component. The strapping mechanism of the device comprises an inferior strap (axillary strap), the axillary pouch, and the compression strap (deltoid strap).

The garment components of the brace are designed such that they cover the wearer's chest, shoulder, arm and axillary areas. The brace is donned by placing the arm of the injured shoulder through the sleeve component of the garment and pulled superiorly so that the shoulder and axillary components of the brace are securely in place. The chest component is then secured by hook type material to the opposite side of the wearer's torso and securely fastened. The inner portion of the garment is a rubberized material to assist in providing control and stability. The outer portion is made of a loop type material so that the strapping mechanism may hook to the garment component.

The strapping mechanism is fixated to the garment component. The axillary pouch and the inferior strapping mechanism are continuous. The axillary pouch is a diamond type shape, which is made of a different stretchable material similar to Lycra for comfort and support of the inferior capsule in the axillary area. The inferior strapping mechanism is comprised of two separate straps, one anterior one posterior, are fixated to either side of the axillary pouch. The axillary pouch is in turn fixated to the axillary portion of the garment component. Each strap (one anterior and one posterior to the shoulder joint) of the inferior strapping mechanism is pulled superiorly which in turn causes the axillary pouch to become taught in the axillary area. The amount of tension can be controlled according to comfort. The anterior and posterior portion of the straps are then criss-crossed in the area of the acromioclavicular joint of the shoulder and pulled in an inferior direction. The anterior portion of the inferior strapping mechanism is then fastened by hook type material to the posterior portion of the garment component crossing the mid-thoracic spine. The posterior portion of the inferior strapping mechanism is then fastened by hook type material to the anterior portion of the garment component crossing the mid-sternal region.

The deltoid strap is fixated firmly to the sleeve portion of the garment component in the area of the deltoid tubercle. With equal tension directed at both ends of the strap in a horizontal direction, each end of the strap is fastened with a hook-typed material to the garment component of the shoulder stabilizer. One portion of the strap positioned anteriorly and one posteriorly on the garment component. Compression is then provided to the shoulder joint.

Therefore the objects of the present invention include to provide a shoulder brace which restrains the humeral head from anterior, posterior and inferior translation; to provide such a brace which applies compression to the glenohumeral joint; to provide such a brace which stimulates proprioceptive awareness of the glenohumeral joint; to provide such a brace whereas the criss-cross fashion of the strapping mechanism provides compression to the acromioclavicular joint; to provide such a brace which is comprised of one piece construction; to provide such a brace which is light-weight; to provide such a brace which has an axillary pouch for inferior support of the glenohumeral joint; to provide such a brace in which the tension of the inferior strapping mechanism is adjustable; to provide such a brace in which the tension of the compression strap is adjustable; to provide such a brace which provides support and compression of the glenohumeral joint; to provide such a brace which allows freedom of movement to the individual; to provide such a brace which applicable to multiple glenohumeral instabilities; to provide such a brace which has ease of application; and to provide such a brace which provides comfort to the individual when applied.

Other objects and advantages will become apparent from the following description of the brace and the accompanying drawings.

BRIEF DESCRIPTIONS OF THE DRAWINGS

DEFINITIONS

Acromioclavicular Joint: The joint formed between the acromion process of the scapula and the distal end of the clavicle.
Glenohumeral Joint: The joint formed by the humeral head with the glenoid fossa.
Anterior: Refers to the ventral or front surface of an object.
Inferior: Refers to a direction toward the feet.
Lateral: Refers to the furthest away from the midline of an object.
Posterior: Refers to the dorsal or back surface of an object.
Superior: Refers to a direction toward the head.

DETAILED DESCRIPTION OF THE INVENTION

Figure 1:
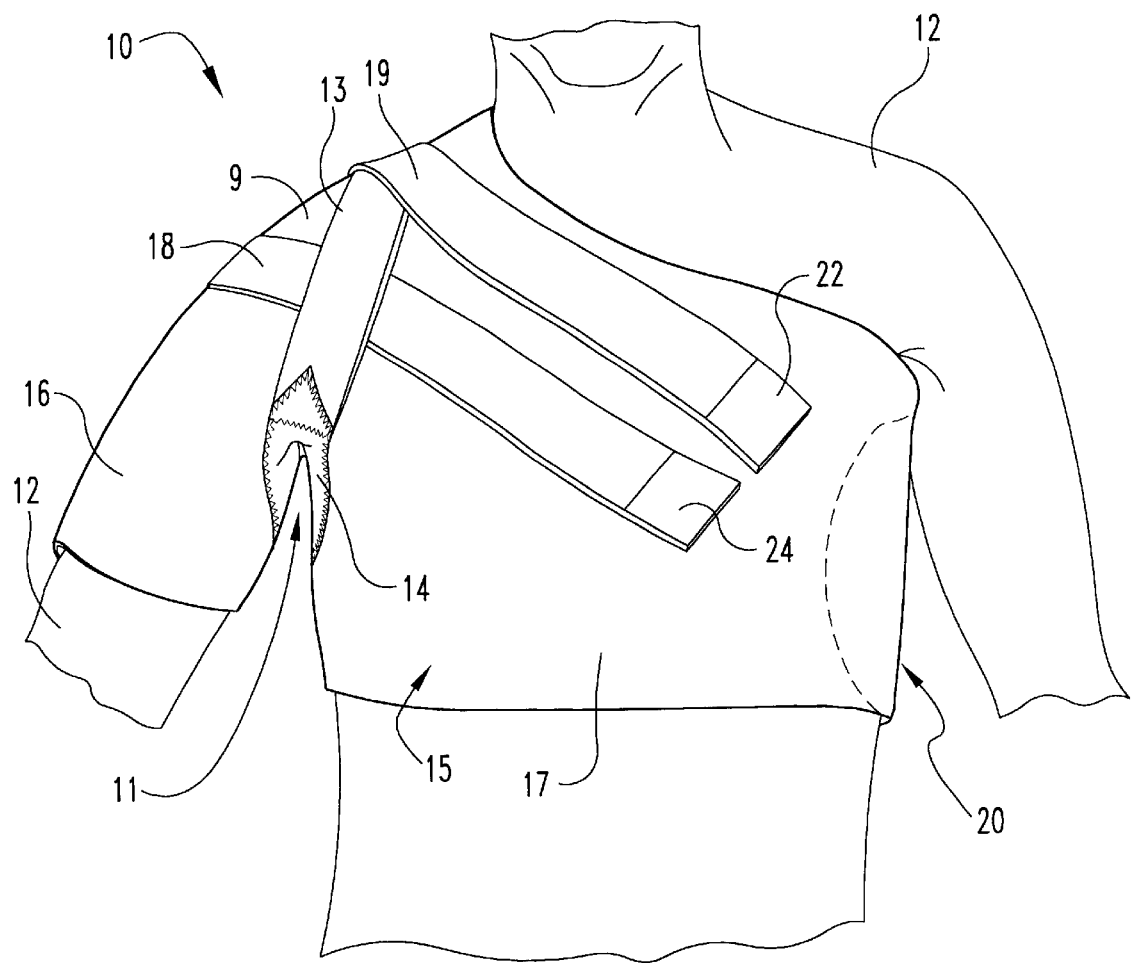
FIG. 1 is a frontal view of the shoulder stabilizing brace with attached strapping mechanism.

FIG. 1 refers to the shoulder stabilizing brace 10 from a frontal view for use in stabilizing the shoulder of the wearer 12. The shoulder stabilizing device 10 comprises a garment 15 that includes a chest component 17, shoulder component 9, axillary component 11, and upper arm (sleeve) component 16. The strapping mechanism of the device 10 comprises inferior straps (axillary straps) 13, 19, the axillary pouch 14, and the compression strap (deltoid strap) 18. This brace 10 is symmetrical to allow it to be devised for either shoulder. The design of the brace 10 will preferably be available in different sizes to accommodate the dimensions of the individual wearer 12. A fastener 20 constructed of a material such as Velcro secures the chest portion 17 of the brace 10. It allows for adjustment based on comfort and security of fit for the individual wearer 12.

The garment portion 15 of the brace 10 is preferably constructed of a thin neoprene material. The exterior side of the garment 15 will have a hook sensitive material. This allows the hook and loop-type fasteners to be directly applied to the brace 10. The interior side of the garment 15 is constructed of the thin neoprene material without the hook sensitive material to reduce heat buildup. The neoprene material grips the skin, which minimizes translation of the brace 10 on the wearer 12. The straps, both axillary straps 13, 19 and deltoid strap 18, are also made of the neoprene material with hook and loop-type closures 22, 24 at the free ends of the straps 13, 19, 18.

The seams of the brace 10 are located at the superior border of the upper arm 16 and shoulder 9 components of the garment 15 as well as the inferior portion of the upper arm 16 and lateral chest 17 component. Stitching or some other suitable means may secure the seams. This also applies to the method of securing the strapping mechanism.

Figure 2:
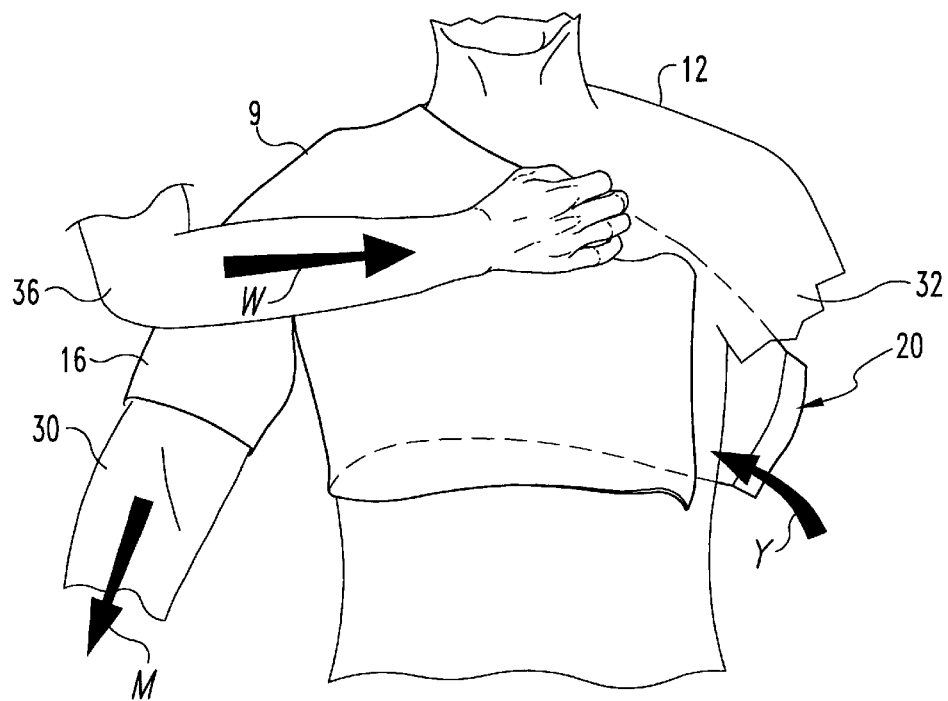
FIG. 2 is an illustration of the application of the garment portion of the device to a wearer.

FIG. 2 illustrates the application of the garment portion 15 of the device 10 to the wearer 12. The wearer 12 inserts an arm 30 into the upper arm component 16 until the shoulder component 9 is positioned over the shoulder using a force in direction M. The wearer 12, or assistant 36, then pulls in direction W to position the brace 10 across the chest using the wearer's free arm 32. While maintaining the force in direction W, the wearer 12 then secures the fastener 20 with the wearer's arm 30 now located in the sleeve component 16, with a pull in direction Y.

Figure 3:
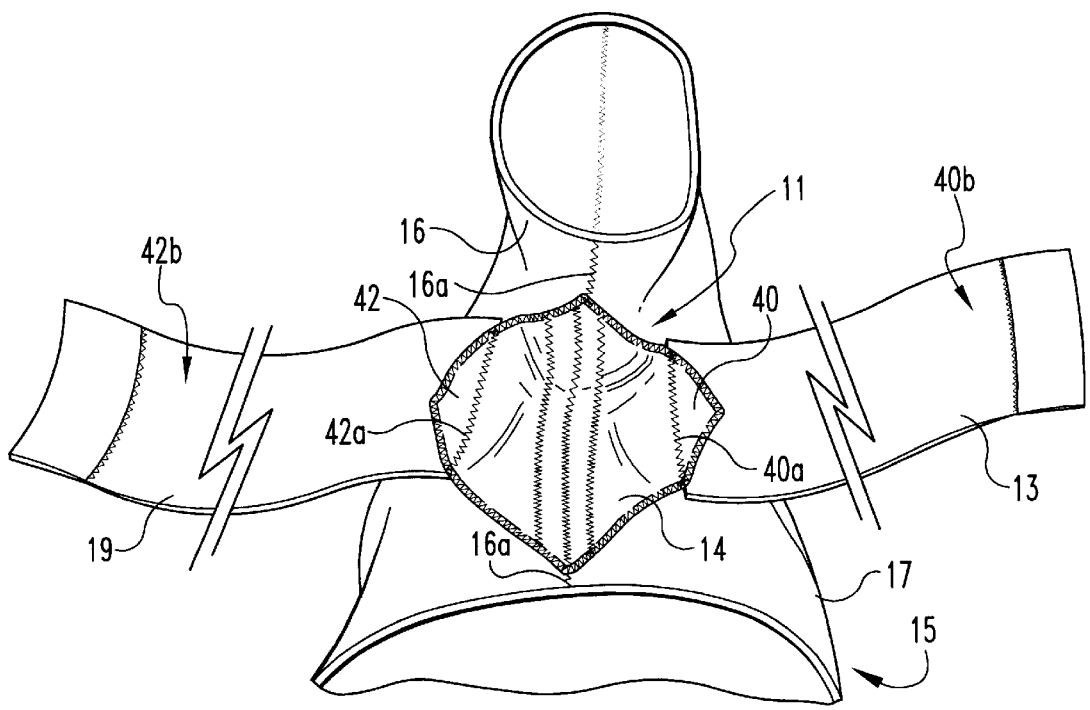
FIG. 3 is a partial view of the axillary pouch with attached axillary straps.

FIG. 3 examines the axillary pouch 14. The axillary pouch 14 is secured to the axillary component 11 of the garment 15 along the seam 16a of the inferior upper arm 16 and lateral chest 17 component. The axillary pouch 14 does not extend to the edges of the upper arm 16 and chest 17 component. Approximately one-inch remains on either side of the garment 15. The axillary pouch 14 is diamond in shape, and the two free ends 40, 42 of the axillary pouch 14 are attached to the anterior 13 and posterior 19 axillary straps by seams 40a, 42a. The material used for the axillary pouch 14 is a thick Lycra material that allows the pouch 14 to be flexible while still providing support to the inferior capsule of the shoulder.

Figure 4A:
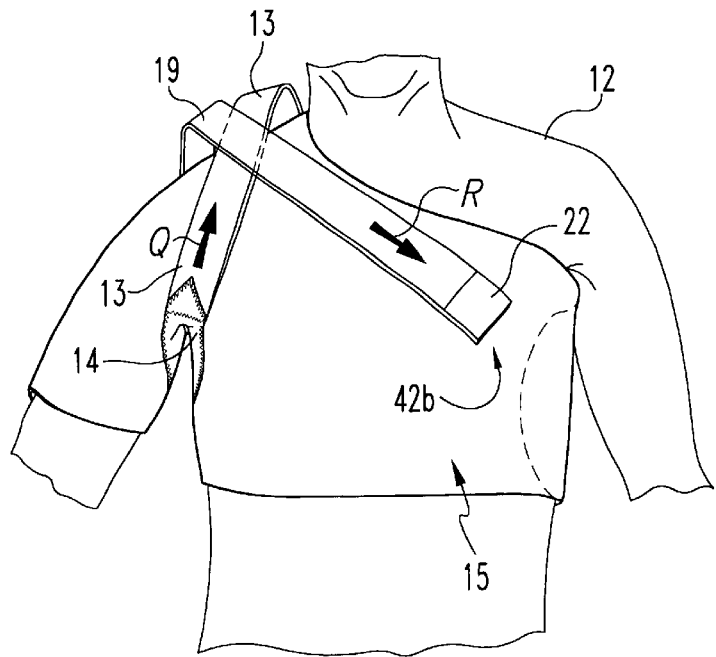
FIG. 4a is a frontal view of the axillary straps attachments to the garment.
Figure 4B:
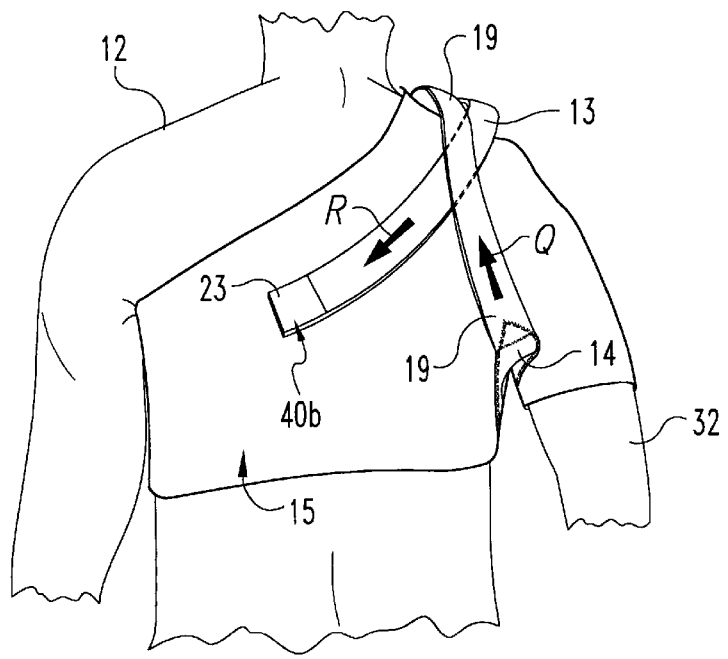
FIG. 4b is a posterior view of the axillary straps attachments to the garment.

FIGS. 4a and 4b illustrate the method of application of the inferior (axillary) straps 13, 19. Using pressure directed superiorly (direction Q), the distal ends 40b, 42b of the axillary straps 13, 19 are crossed over the acromioclavicular joint. Once the straps 13, 19 have crossed the acromioclavicular joint, equal pressure is directed in an inferior direction (direction R). The anterior axillary strap 13 is secured to the posterior side of the chest component 17 of the garment 15 with hook and loop closure 23 while the posterior axillary strap 19 is fastened in the manner to the anterior side of the garment 15 with the hook and loop closure 22. This configuration assists in stabilizing the inferior capsule of the shoulder, which can assist in treating multidirectional, anterior, posterior, and inferior shoulder instabilities. Acromioclavicular injuries can also be treated using the criss-cross design of the axillary straps 13, 19.

Figure 5A:
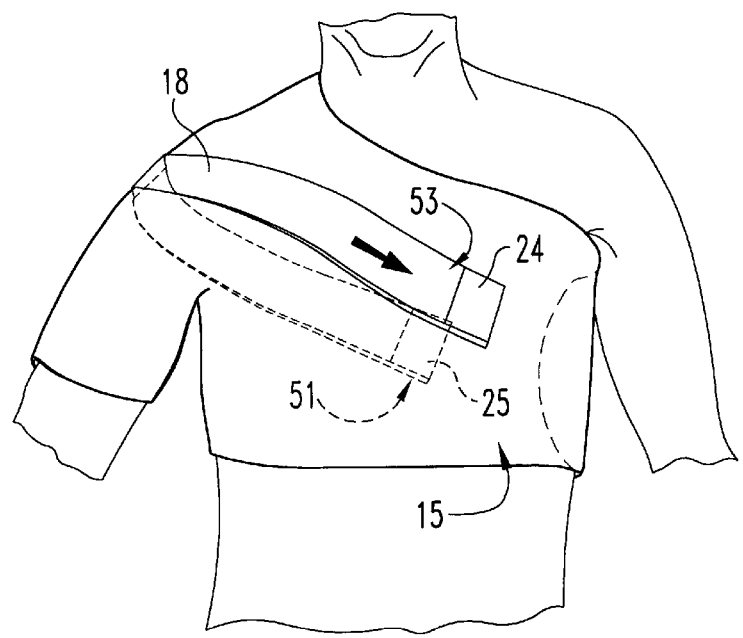
FIG. 5a is a frontal view of the deltoid strap attachment to the garment.
Figure 5B:
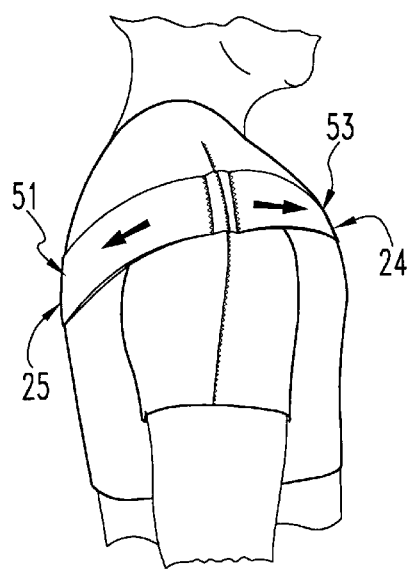
FIG. 5b is a side view of the deltoid strap attachment to the garment.
Figure 1:
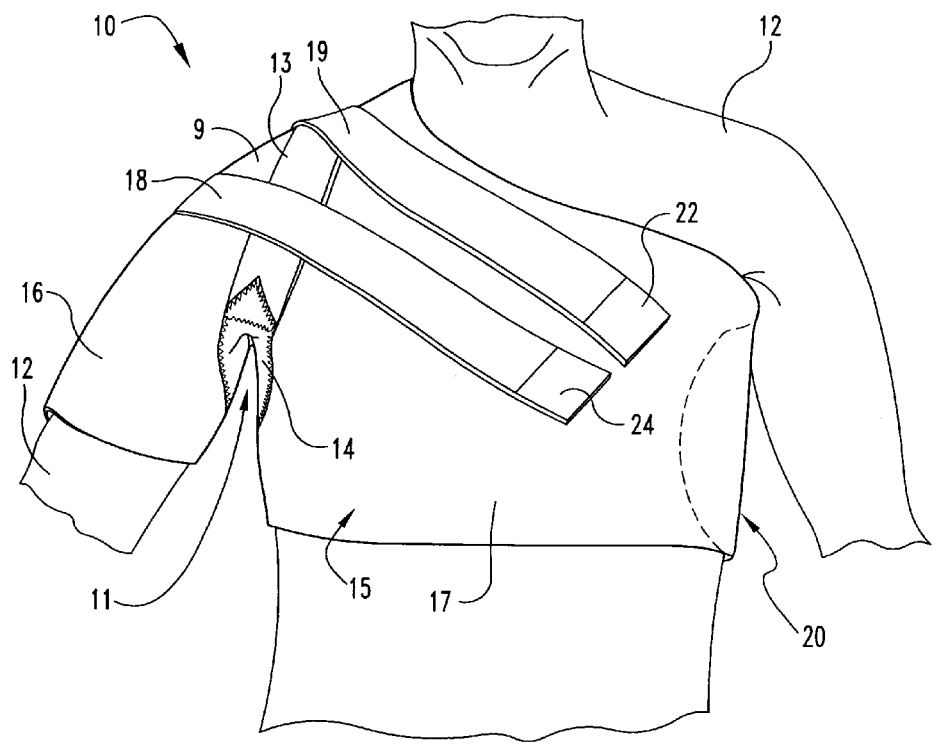

FIGS. 5a and 5b refer to the application of the compression (deltoid) strap 18. The deltoid strap 18 is attached longitudinally to the superior seam of the shoulder 9 and upper arm 16 component of the garment 15 at the deltoid insertion of the shoulder. With equal tension directed at both ends 51, 53 of the strap 18, the deltoid strap 18 is secured across the chest in a horizontal fashion. One end 51 of the strap 18 is fastened to the posterior side of the garment 15 while the other end 53 is fastened to the anterior side of the garment 15 with the hook and loop closures 24, 25. This strap 18 provides compression to the shoulder designed to stabilize and provide proprioceptive input to the shoulder for multidirectional, anterior, posterior, and inferior shoulder instabilities.

Although the invention has been described with respect to specific preferred embodiments, other embodiments utilizing the concepts of the present invention are possible without departing from the scope of the invention. The invention is not intended to be limited to the specific embodiments but the invention is defined by the claims below.

We claim:

1. A method of stabilizing the shoulder joint of an individual with anterior, inferior, posterior or multi-directional instability comprising the following steps:

(a) providing a stabilizing garment that includes a chest component, shoulder component, axillary component, and an upper arm sleeve component, inserting the individual's arm into the upper arm component, and securing the garment about the torso with hook and loop-type fasteners;

(b) further providing an axillary pouch fixated to the garment component at the inferior portion of the upper arm component and along the lateral portion of the chest component, said axillary pouch being diamond in shape with two free ends for attachment of an inferior strapping mechanism, thereby creating reinforcement to the inferior capsule of the shoulder joint;

(c) further providing an inferior strapping mechanism comprised of two equal straps fixated to the axillary pouch at its two free ends, and then criss-crossing each strap on the superior portion of the shoulder joint and securing the straps to the garment with hook and loop-type fasteners with one strap secured anteriorly, the other posteriorly, with equal pressure, thereby providing shoulder stability by reinforcing the inferior capsule; and (d) fixing deltoid strap longitudinally to the sleeve component of the garment, whereby two equal portions of the strap can be pulled across the torso and attached to the garment with hook and loop-type fasteners, thereby creating compression to the shoulder joint.

2. The method of claim 1 wherein the garment has an inside surface constructed of a rubberized material for gripping the skin and an outside surface constructed of a loop type material for attachment of the hook and loop-type fasteners.

3. The method of claim 1 wherein the axillary pouch is constructed of a stretchable material.

4. The method of claim 1 wherein the inferior strapping mechanism has an inside surface constructed of a rubberized material for gripping and an outside surface of a loop-type material for attachment of the hook and loop-type fastener.

5. The method of claim 1 wherein the deltoid strap has an inside surface constructed of a rubberized material for gripping and an outside surface of a loop-type material for attachment of the hook and loop-type fastener.

6. A stabilizing shoulder brace to stabilize the joint of an individual with anterior, inferior, posterior or multi-directional instability comprising a garment that traverses the individual's torso that includes a chest component, shoulder component, axillary component, and an upper arm sleeve component into which the individual inserts an arm, an axillary pouch fixated to the garment at the inferior portion of the upper arm component and along the lateral portion of the chest component, the axillary pouch being diamond in shape with two free ends for attachment of an inferior strapping mechanism, thereby creating reinforcement to the inferior capsule of the shoulder joint; wherein the inferior strapping mechanism is comprised of two equal length straps fixated to the axillary pouch at its two free ends, with each strap crisscrossed on the superior portion of the shoulder joint and secured to the garment by hook and loop-type fasteners, whereby one strap is secured anteriorly, and the other posteriorly thereby providing shoulder stability by reinforcing the inferior capsule; and a deltoid strap fixed longitudinally to the upper arm sleeve component of the garment so that equal portions of the deltoid strap can be pulled across the individual's torso and attached to the garment by hook and loop-type fasteners thereby creating compression to the shoulder joint.

7. The brace of claim 6 wherein the garment has an inside surface constructed of a rubberized material for gripping the skin and an outside surface constructed of a loop type material for attachment of hook and loop-type fasteners.

8. The brace of claim 6 wherein the axillary pouch is constructed of a stretchable material.

9. The brace of claim 6 wherein the inferior strapping mechanism has an inside surface constructed of a rubberized material for gripping and an outside surface of a loop type material for attachment of hook and loop-type fasteners.

10. The brace of claim 6 wherein the deltoid strap has an inside surface constructed of a rubberized material for gripping and an outside surface of a loop-type material for attachment of hook and loop-type fasteners.

11. A method of providing stabilization and compression to an individual with anterior, inferior, posterior or multidirectional instabilities in a shoulder comprising providing a garment that includes a chest component, shoulder component, axillary component, and an upper arm sleeve component into which the individual inserts an arm;

applying the garment portion of the brace to the individual by inserting an arm into the upper arm component until the shoulder component is positioned over the shoulder and pulling the garment horizontally to cover the individual's torso and fastening the garment on the torso;

applying inferior axillary straps using equal pressure directed superiorly, with the distal ends of opposing axillary straps crossed over the individual's acromioclavicular joint, and once crossed, pulling the straps inferiorly, and securing the anterior axillary strap to the posterior side of the chest component of the garment while the posterior axillary strap is fastened to the anterior side of the garment with the hook and loop-type fasteners, whereby this configuration assists in stabilizing the inferior capsule of the shoulder, which assists in treating anterior, posterior, inferior, and multidirectional shoulder instabilities and which also treats acromioclavicular injuries by using the criss-cross design of the axillary straps; and applying a compression deltoid strap with equal tension directed at both ends of the strap across the torso in a horizontal fashion, with one end of the strap fastened to the posterior side of the garment and the other end fastened to the anterior side of the garment with hook and loop-type fasteners, thereby providing compression to the shoulder designed to stabilize and provide proprioceptive input to the shoulder for anterior, posterior, inferior, and multidirectional instabilities.

* * * * *

UNITED STATES PATENT AND TRADEMARK OFFICE
CERTIFICATE OF CORRECTION

PATENT NO.    : 6,398,746 B2
DATED         : June 4, 2002
INVENTOR(S)   : Meghan Bramlage and Patti J. Hunker It is certified that error appears in the above-identified patent and that said Letters Patent is hereby corrected as shown below:

<u>Title page, Item [54] and Column 1, line 1,</u>
Please delete "SHOULDERS STABILIZING BRACE" and insert in lieu thereof
-- SHOULDER STABILIZING BRACE --.

<u>Drawing,</u>
Sheet 1, please delete Fig. 1 and insert in lieu thereof the attached Fig. 1.

Signed and Sealed this

Thirteenth Day of May, 2003

JAMES E. ROGAN
*Director of the United States Patent and Trademark Office*